United States Patent [19]

Schally et al.

[11] Patent Number: 4,725,577
[45] Date of Patent: Feb. 16, 1988

[54] BIOLOGICALLY ACTIVE LYSINE CONTAINING OCTAPEPTIDES

[75] Inventors: Andrew V. Schally, Metairie; Ren Z. Cai, New Orleans, both of La.

[73] Assignee: Administrators of the Tulane Educational Fund, New Orleans, La.

[21] Appl. No.: 843,539

[22] Filed: Mar. 28, 1986

Related U.S. Application Data

[63] Continuation-in-part of Ser. No. 727,105, Apr. 25, 1985, Pat. No. 4,650,787.

[51] Int. Cl.$^4$ .......................... H61K 37/02; C07K 7/06
[52] U.S. Cl. .......................................... 514/11; 514/15; 530/328
[58] Field of Search ................ 530/328, 327, 329, 311; 514/11, 15

[56] References Cited

U.S. PATENT DOCUMENTS

| 4,209,426 | 6/1980 | Sarantakis | 530/311 |
| 4,282,143 | 8/1981 | Sarantakis | 530/311 |
| 4,440,904 | 4/1984 | Sarantakis | 530/328 |
| 4,451,394 | 5/1984 | Sarantakis | 530/327 |
| 4,496,543 | 1/1985 | Bauer et al. | 530/329 |

Primary Examiner—Delbert R. Phillips
Attorney, Agent, or Firm—Omri M. Behr

[57] ABSTRACT

Novel compositions of the formula

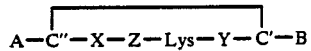

wherein
A represents an L, D or DL amino-acid selected from the group consisting of Ala, Val, Phe, p-Cl-Phe, Trp, Pro, Ser, Thr, Glu, Gly, Beta Ala, Abu, N-Me Ala, 5-F-Trp, 5-Br-Trp, 5-Cl-Trp, their acetylated derivatives or a pharmaceutically acceptable acid addition salt thereof;
B represents an L, D or DL amino acid amide selected from the group consisting of Thr $NH_2$, Val $NH_2$, Pro $NH_2$, HO-Pro $NH_2$, Ser $NH_2$, Tyr $NH_2$, Trp $NH_2$, 5-F-Trp $NH_2$, For-Trp $NH_2$, Ala $NH_2$, Gly $NH_2$, Me Ala $NH_2$;
X represents L-Phe or L-Tyr,
Y represents L-Thr or L-Val;
Z is L, D or DL-5-F-Trp, 5-Br-Trp, 5-Cl-Trp, 5-I-Trp or D-Trp; and
C" and C' represent L or D Cys, Abu, Asp or Lys; and the pharmaceutically acceptable acid addition salts thereof; are useful as agents for inhibiting the release of growth hormone, for the treatment of gastrointestinal disorders and for therapy of certain cancers and the management of diabetes. These biologically active octapeptides all possess a terminal amino acid amide at position 8 and are prepared by solid phase methods.

15 Claims, 1 Drawing Figure

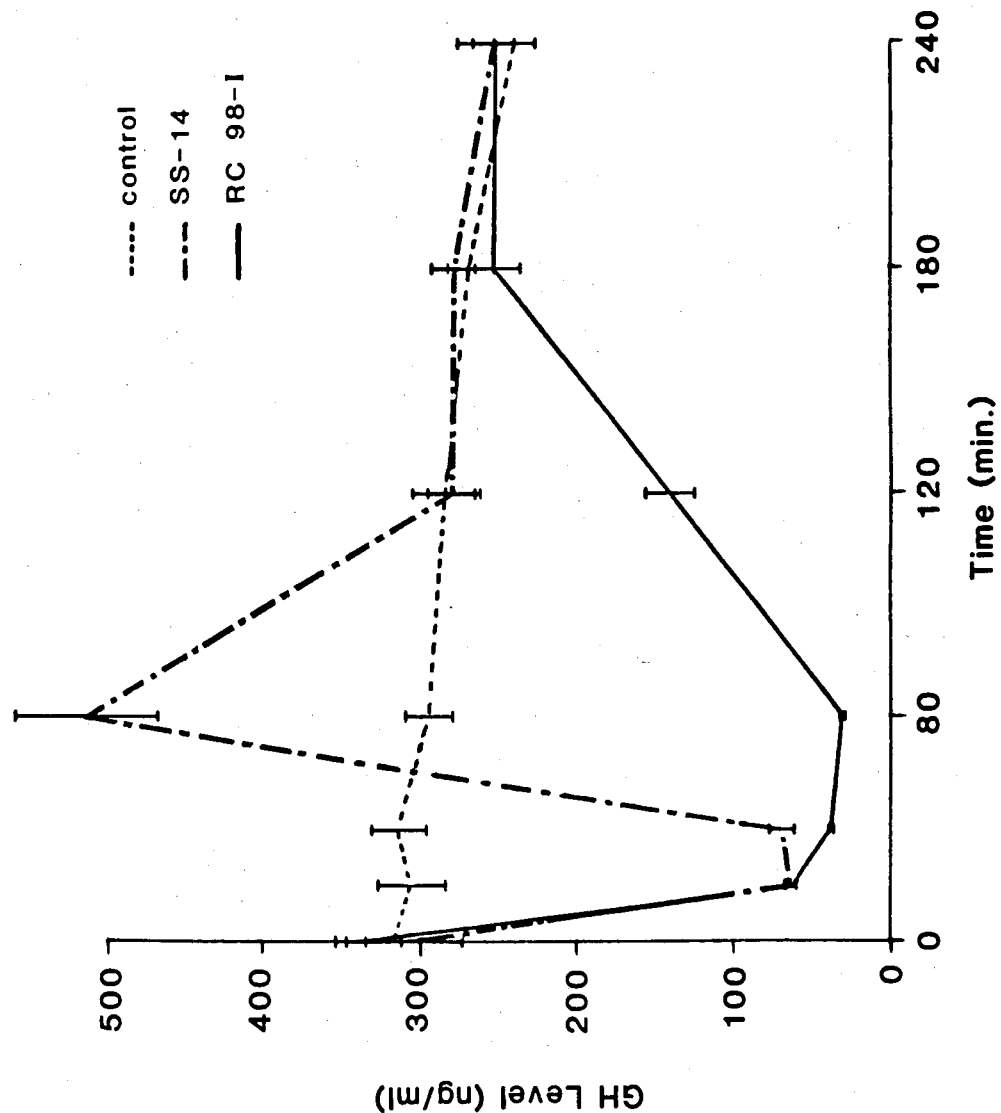

BIOLOGICALLY ACTIVE LYSINE CONTAINING OCTAPEPTIDES

RELATED APPLICATIONS

This application is a continuation-in-part of our co-pending application, Ser. No. 727,105, filed Apr. 25, 1985, now U.S. Pat. No. 4,650,787.

BACKGROUND OF THE INVENTION

Somatostatin is a cyclic tetradecapeptide which inhibits the secretion of pituitary growth hormone. Several analogs of somatostatin have been previously described. Verber et al., *Nature*, 292, 55, (1981) has reported the synthesis and the activity of a cyclic hexapeptide analog obtained by replacing 9 of the 14 aminoacids of somatostatin with a single proline. Additionally, the same group has reported hexapeptide derivatives of high potency, *Life Sciences*, 34, 1371 (1984). Bauer, et al., in "Peptides" 1982, p. 583, Ed. K. Blaha, P. Malon—1983 by Walter de Gruyter & Co., Berlin, New York, describe the synthesis and activity of octapeptide analogs. (cf. also *Life Sciences*, 31, 1133, L982)).

In general, the abbreviations used herein for designating the amino acids and the protective groups are based on recommendations of the IUPAC-IUB Commission of Biochemical Nemenclature, see *Biochemistry*, 11, 1726–1732 (1972). For instance, Abu, Ala, Gly, Cys, Lys, Asn, Asp, Phe, Trp, L-Trp, D-Trp, DL-Trp, D-5-Br-Trp, L-5-F-Trp, Thr and Ser represent the "residues" of α-aminobutyric acid, L-alanine, glycine, L-cysteine, L-lysine, L-asparagine, L-aspartic acid, L-phenylalanine, L-tryptophan, L-tryptophan, D-tryptophan, DL-tryptophan, D-5-bromotryptophan, L-5-fluorotryptophan, L-threonine and L-serine, respectively. The term "residue" refers to a radical derived from the corresponding alpha-amino acid by eliminating the hydroxyl of the carboxyl group and one hydrogen of the alpha-amino group.

SUMMARY OF THE INVENTION

The present invention relates to analogs of the tetradecapeptide somatostatin. More particularly, this invention relates to octapeptide somatostatin analogs of the formula I:

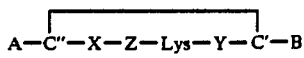
(I)

wherein

A is an L, D or DL amino acid selected from the group consisting of Alanine (Ala), valine (Val), phenylalanine (Phe), para-chloro-phenylalanine (p.Cl Phe), tryptophan (Trp), proline (Pro), serine (Ser), Threonine (Thr), tyrosine (Tyr), glutamic acid (Glu), beta alanine (Beta Ala), α-aminobutyric acid (Abu), N-methylalanine (N-Me Ala), 5-fluorotryptophan (5-F Trp), 5-bromotryptophan (5-Br Trp), 5-chlorotryptophan (5-Cl Trp), their acetylated derivatives or a pharmaceutically acceptable acid addition salt thereof;

B is an L, D or DL amino acid selected from the group consisting of threonine amide (Thr NH$_2$), valine amide (Val NH$_2$), proline amide (Pro NH$_2$), hydroxyproline amide (HO Pro NH$_2$), serine amide (Ser NH$_2$), tyrosine amide (Tyr NH$_2$), tryptophan amide (Trp NH$_2$), 5-fluorotryptophan amide (5-F Trp NH$_2$), formyl tryptophan amide (For Trp NH), alanine amide (Ala NH$_2$), glycine amide (Gly NH$_2$) and methylalanine amide (Me Ala NH$_2$);

X is L-phenylalanine (L-Phe) or L-tyrosine (L-Tyr);

Y is L-threonine (L-Thr) or L-valine (L-Val);

Z is L, D or DL 5-halo-tryptophan, in which the halogen (Halo-) is fluorine, chlorine, bromine or iodine, or D-tryptophan (D-Trp); and C″ and C′ are L or D-cysteine (Cys), α-aminobutyric acid (Abu), aspartic acid (Asp) or lysine (Lys); and the pharmaceutically acceptable acid addition salts thereof. Certain derivatives are within the scope of this invention. Thus Cys alone means D-cysteine in the sulfhydryl form, whereas a bridge between two Cys groups should be read as a disulfide bridge unless there is any supplemental indication. MBz is p-methoxy benzyl, 2-ClZ is 2-chlorocarbobenzyloxy, similarly 2-BrZ is the corresponding 2-bromocarbobenzyloxy group. Where such groups appear next to an amino acid, either prior or subsequent, but between hyphens, such a group is a substituent on the aminoacid to which it is adjacent.

Further, the present invention encompasses the novel intermediates which are the reduced forms of the compounds of formula I and methods and compositions utilizing these novel octapeptides for the treatment of various mammalian disorders.

These octapeptides inhibit the release of such hormones as growth hormone, prolactin, insulin, glucagon, gastrin, secretin and cholecystokinin, as well as diminish gastrin-stimulated secretion of gastric acid. These effects may be independent of the administration of other physiologically active compounds or as an effect of the combination of the subject composition with other physiologically active compounds.

The octapeptides of the present invention can thus be used for the treatment of such disease states as diabetic retinopathy, diabetes, ulcers, acute pancreatitis and acromegaly. In addition, where the growth of oncogenic tissue is affected by one of the hormones regulated by octapeptides, these octapeptides can be used in the treatment of such tumors. Such tumors are those such as prostatic adenocarcinomas, mammary carcinomas (influenced by prolactin and growth hormone) as well as insulinomas, gastrinomas, growth hormone and insulin dependent tumors such as chondrosarcomas and osteosarcomas as well as pancreatic ductal and acinar tumors (pancreatic carcinomas) dependent of gastrointestinal hormones.

DESCRIPTION OF THE PREFERRED EMBODIMENTS

The octapeptides of the present invention are encompassed by the above formula I. These octapeptides exist in a cyclic form due to a bridge between the C″ and C′ substituents. This bridge may be a disulfide bridge (—S—S—), a carbon/sulfur bridge (—C—S—), a carbon/carbon bridge (—C—C—) or an amido bridge (—CO—NH—) depending on the method of formation. The reduced forms of the octapeptides of formula I are encompassed by formula I′ below. These reduced forms are intermediates in the process for preparing the compounds of formula I.

Of the compounds of formula I, certain combinations of substituents are preferred. For instance, compounds wherein C″ is Cys, X is Phe, Z is D-Trp, Y is Thr, and C′ is Cys; compounds wherein C″ is Cys, X is Tyr, Z is D-Trp, Y is Val and C′ is Cys; X is Phe, Y is Thr, and C' is Cys; and compounds wherein C" is Cys, X is Tyr, Y is Val, and Cys are preferred compounds.

The octapeptides of this invention are obtainable in the form of the free base or in the form of a pharmaceutically or therapeutically acceptable acid addition salt. The octapeptides in the form of the free bases are readily obtainable from the corresponding acid addition salt by conventional methods, for example, a solution of the acid addition salt is passed through an anionic exchange resin (OH form) to obtain the free base. The free base can also be obtained from the acetic addition salt by repeated lyophilization of the latter salt from aqueous solution. The acetic acid addition salt is readily obtainable from another acid addition salt by treatment with the appropriate ion exchange resin, for example, Sephadex G-15 using 50% acetic acid in the manner described by Coy, et al., *Biochem. Biophys. Res. Commun.*, 1267–1273 (1973).

The octapeptides of this invention can be obtained in the form of a pharmaceutically or therapeutically acceptable acid addition salt either directly from the process of this invention or by reacting the peptide with one or more equivalents of the appropriate acid. Examples of preferred non-toxic salts are those with pharmaceutically or therapeutically acceptable organic acids, e.g., acetic, lactic, succinic, benzoic, salicyclic, methanesulfonic, toluenesulfonic or pamoic acid, as well as polymeric acids such as tannic acid or carboxymethyl cellulose and salts with inorganic acids such as the hydrohalic acids, e.g., hydrochloric acid or sulfuric acid or phosphoric acid.

The octapeptides of this invention can be prepared by solid phase synthesis. The synthesis begins at the C-terminal end of the peptide. The first protected amino acid is linked to the benzhydrylamine resin by reaction of the carboxyl group protected amino acid in the presence of N,N'-dicyclohexylcarbodiimide or N,N'-diisopropylcarbodiimide and 1-Hydroxybenzotriazole (HOBT). The sequential building of the peptide involves the stepwise addition of each amino acid in the N-terminal portion of the peptide chain.

The cleavage of the N-terminal protecting group is accomplished by using trifluoroacetic acid. The other protecting groups present on the peptide chain are stable under the conditions of the cleavage of the N-terminal protecting group. Once the N-terminal deprotection has been effected, the product which results normally will be in the form of the addition salt of trifluoroacetic acid. The free terminal amino compound is formed by treating with a mild base, typically a tertiary amine such as triethylamine of diisopropylethylamine. The peptide resin is then ready for the coupling with the next amino acid which has a free carboxyl but which is protected at the alpha-amino group.

Once the desired amino acid sequence is prepared, the resulting peptide is removed from the resin support. This is accomplished by the treatment of the peptide resin with hydrogen fluoride. The hydrogen fluoride cleaves the peptide from the resin and, in addition, it cleaves all remaining protecting groups except formyl group of Trp. This treatment of hydrogen fluoride is carried out in the presence of m-cresol and anisole which are found to inhibit the potential alkylation of certain amino acids present in the peptide chain.

When the cleavage reaction is accomplished, the product is obtained in the reduced form, i.e., of the formula I':

$$A-C''-X-Z-Lys-Y-C'-B \quad (I')$$

wherein A, C", X, Z, Y or C' and B are as hereinbefore defined. Oxidation will generate a disulfide bridge and allow the products to be obtained in the cyclized form of formula I. Use of well known coupling techniques will yield, in place of a disulfide bridge, an amido bridge between C" and C'.

Although the selection of the particular protecting groups to be employed in preparing the compounds of this invention remains a matter well within one ordinarily skilled in the art, it should be recognized that the proper selection of the protecting groups is dependent upon the particular succeeding reactions which must be carried out. Thus, the protecting group of choice must be one which is stable both to the reagents and under the conditions employed in the succeeding steps of the reaction sequence. For example, as already discussed hereinabove, the particular protecting group employed must be one which remains intact under the conditions which are employed for cleaving the alpha-amino protecting group of the terminal amino acid residue of the peptide fragment in preparation for the coupling of the next succeeding amino acid fragment to the peptide chain. It is also important to select as protecting group, one which will remain intact during the building of the peptide chain and which will be readily removable upon completion of the synthesis of the desired octapeptide product. All of these matters are well within the knowledge and understanding of one ordinarily skilled in the art.

The octapeptides produced by the process of this invention, as well as their corresponding pharmaceutically or therapeutically acceptable acid addition salts, are useful due to their possession of the pharmacological activity of the natural tetradecapeptide somatostatin. Such activity is demonstrated readily in pharmacological tests such as a modification of the in vitro method of Saffran and Schally, *Can. J. Biochem. Physiol.*, 33, 405 (1955) as given in Schally, et al., *Biochem. Biophys. Res. Commun.*, 52, 1314 (1973) and River, et al., *C.R. Acad. Sci. Paris*, Ser. D., 276, 2337 (1973).

The ability of the octapeptides of this invention to inhibit hormone release in vitro is demonstrated by the method described by Meyers, et al., *Biochem. Biophys. Res. Commun.*, 74, 630 (1977). In this method, the octapeptides of this invention are shown to inhibit the release of radioimmunoassayable growth hormone and prolactin in vitro from enzymatically dispersed rat anterior pituitary cells prepared as described by Labrie, et al., *Sixth Karolinska Symp. on Res. Meth. in Reprod. Endocrinol.*, (E. Diczfalusy, Ed.). pp 301–328 (1973). Following four days in culture, the cells are washed and incubated for five hours at 37° C. in Dulbecco-modified Eagle's medium in the presence or absence of increasing concentrations of each octapeptide analog. Growth hormone and prolactin levels are determined by radioimmunoassay, using methods described by Birge, et al., *Endocrinol.*, 81, 195–204 (1967) for rat growth hormone and Niswender, et al., *Proc. Soc. Exp. Biol. Med.*, V 130, 793 (1969) for prolactin. NIAMDD Rat GH and prolactins RIA kits here used as standards. The dose required for a 50% inhibition of growth hormone release (ED 50) is calculated for each analog by the method of Rodbard, *Endocrinol.*, 94, 1427–1437 (1974).

In vitro inhibition of growth hormone and prolactin is also measured in a pituitary cell superfusion system as described by Vigh and Schally (Peptides, Vol. 5, Suppl. 1., p. 241-247). Adult male or female Sprague-Dawley strain rats are decapitated for each experiment. The anterior pituitaries are cut into small pieces and incubated in a Dubnoff incubator for 45 minutes at 37° C. in 10 ml. of oxygenated Medium 199 (GIBCO) containing 0.5% collagenase, 0.25% bovine serum albumin (BSA), and 50 μ/ml Gentamicin Sulphate. After this incubation, the fragments can be easily dispersed into single cells by repeated suction and expulsion from a Gilson Pipetman. After 30 to 60 Pipetman operations, the tissue falls apart. The cell suspension is centrifuged at room temperature for 10 minutes at 100 g. The cell pellet is then resuspended in 1.0 ml. of medium. A small aliquot is diluted for counting the cells and the rest of the suspension is divided into 4 equal volumes. Each volume (containing about $5 \times 10^6$ cells) is mixed with 0.5 ml. Sephadex G-15 which has been equilibrated with previously oxygenated medium. The mixture of pituitary cells and Sephadex is transferred into four chambers of the superfusion apparatus consisting of a number of 1 ml. plastic syringe barrels (modified by cutting off their distal end) and mounted vertically in a plexiglas holder which was kept at 37° C. by circulating water. The flow through the system (0.5 ml. min) is controlled with a multichannel peristaltic pump (Vigh and Schally, Peptides, Vol. 5, Suppl. 1, p. 214-247. Rat prolactin and rat GH were measured in aliquots of superfusates by RIA to determine either basal or inhibited secretion.

The in vivo growth hormone bioassay utilized is as follows:

Male Charles River CD rats (200-300 g.) with free access to food and water were anesthetized with sodium pentobarbital (60 mg.kg intraperitoneally). Thirty minutes later saline or octapeptide is injected subcutaneously and blood samples are drawn from the jugular vein 15 minutes after subcutaneous injection. The plasma is separated and assayed for growth hormone by RIA as described above. This in vivo bioassay is a modification of the methods used by Schally, et al., "Hypothalamic Peptide Hormones: Basic and Clinical Studies", "Hormonal Proteins and Peptides", C. H. Li, ed. Academic Press, N.Y. 7: 1-54, 1978; Meyers, C. A., Murphy, W. A., Redding T. W., Coy, D. H. and Schally, A. V., Proc. Natl. Acad. Sci., USA 77: 6171, 1980; Murphy, W. A., Meyers, C. A. and Coy, D. H., Endoc. 109: 491, (1981) as well as Veber et al., Pro. Natl. Acad. Sci., USA 75: 2636-2640 (1978). For some analogs, doses as low as 0.02 μg/100 g. or even 0.005 μg/100 g. are active. The potency of the octapeptides of this invention relative to somatostatin is illustrated in Tables A, B and C. Single dose assays are shown in Table A and 4 point assays at 2 dose levels in Tables B and C.

TABLE A

Single Dose Assays of Somatostatin Octapeptide Analogs vs. Somatostatin 14. (SS-14) Inhibition of GH Release

| Substance Tested | Amount Injected/100 g.B.W. (μg) | GH-Level (ng/ml) mean ± SEM |
|---|---|---|
| RC-121-2H | 0.05 μg | 61 ± 17* |
| RC-114-2H | 0.05 μg | 55 ± 10* |
| SS-14 | 2.00 μg | 95 ± 31* |
| CONTROL | SALINE | 754 ± 155 |
| RC-122-2H | 0.20 μg | 23 ± 3* |
| SS-14 | 2.00 μg | 50 ± 12* |
| CONTROL | SALINE | 374 ± 69 |

*p (0.01 vs. Control (Duncan's test).
RC-121-2H = D-Phe—Cys—Tyr—D-Trp—Lys—Val—Cys—Thr—NH$_2$.
RC-114-2H = D-Phe—Cys—Tyr—D-Trp—Lys—Val—Cys—Ser—NH$_2$.
RC-122-2H =

$$\text{D-Phe—Cys—Tyr—D-Trp—Lys—Val—Cys—Trp—NH}_2,$$
with FOR on Tyr and FOR on Trp where Cys = crysteine; Trp = N—Formyl-Tryptophan.

TABLE B

Four-Point Assay of GH-Release Inhibition Activity of Somatostatin Octapeptides Analogs vs. Somatostatin-14 in Rats

| Substance Tested | Amount Injected/100 g.B.W. (μg) | GH-Level (ng/ml) mean ± SEM |
|---|---|---|
| CONTROL | SALINE | 277 ± 166 |
| SS-14 | 0.4 μg | 86 ± 16 |
| SS-14 | 1.6 μg | 47 ± 17 |
| RC-121-2H | 0.02 μg | 39 ± 10 |
| RC-121-2H | 0.08 μg | 21 ± 4 |
| RC-114-2H | 0.02 μg | 44 ± 11 |
| RC-114-2H | 0.08 μg | 34 ± 9 |

RC-121-2H vs. SS-14: M = 0.7709, Antilog M = 5.9, Potency = 118-times vs. SS-14,
RC-114-2H vs. SS-14: M = 0.6757, Antilog M = 4.74, Potency = 95.8-times vs. SS-14,
RC-121-2H = D-Phe—Cys—Tyr—D-Trp—Lys—Val—Cys—Thr—NH$_2$,
RC-114-2H = D-Phe—Cys—Tyr—D-Trp—Lys—Val—Cys—Ser—NH$_2$, Factorial statistical analyses and calculation of potencies in 4 point design assays were carried out by the method of Bliss and Marks (Bliss, C. I. and Marks; H. P.: Quart. J. Pharm. and Pharmacol. 12, 82 and 182, 1946), and Pugsley, (L. I.: Endocr., 39, 161-176, 1946).

TABLE C

Relative Potencies of Somatostatin and Somatostatin Analogs on Inhibition of GH and Insulin Release in vivo Based on 4-Point Assays

| CODE | PEPTIDE | INHIBITION GH in vivo | POTENCY INSULIN in vivo |
|---|---|---|---|
|  | SS-14 (Somatostatin) | 100 | 100 |
| RC-15 | Ac—p-Cl—D-Phe—Cys—Phe—D-Trp—Lys—Thr—Cys—Thr—NH$_2$ (cyclic Cys-Cys) | 860 |  |
| RC-76-2H | Ac—D-Phe—Cys—Phe—D-Trp—Lys—Thr—Cys—Pro—NH$_2$ | 1070 |  |
| RC-127-2H | D-Val—Cys—Phe—D-Trp—Lys—Thr—Cys—Thr—NH$_2$ | 790 |  |
| RC-138-2H | D-Phe—Cys—Tyr—D-Trp—Lys—Val—Cys—Ala—NH$_2$ | 1570 |  |
| RC-88 | p-Cl—D-Phe—Cys—Phe—C-Trp—Lys—Thr—Cys—Thr—NH$_2$ (cyclic Cys-Cys) | 2130 |  |
| RC-88-II-2H | p-Cl—D-Phe—Cys—Tyr—D-Trp—Lys—Val—Cys—Thr—NH$_2$ | 3020 | 1860 |

TABLE C-continued
Relative Potencies of Somatostatin and Somatostatin
Analogs on Inhibition of GH and Insulin Release in vivo
Based on 4-Point Assays

| CODE | PEPTIDE | INHIBITION GH in vivo | POTENCY INSULIN in vivo |
|---|---|---|---|
| RC-88-II | p-Cl—D-Phe—Cys—Tyr—D-Trp—Lys—Val—Cys—Thr—NH$_2$ (Cys-Cys bridge) | 1740 | |
| RC-122-2H | D-Phe—Cys—Tyr—D-Trp—Lys—Val—Cys—Trp—NH$_2$ (Cys-Cys bridge, FOR on Trp) | 5540 | |
| RC-114-2H | D-Phe—Cys—Tyr—D-Trp—Lys—Val—Cys—Ser—NH$_2$ | 9580 | 440 |
| RC-121-2H | D-Phe—Cys—Tyr—D-Trp—Lys—Val—Cys—Thr—NH$_2$ | 11800 | |
| RC-121 | D-Phe—Cys—Thr—D-Trp—Lys—Val—Cys—Thr—NH$_2$ (Cys-Cys bridge) | 19900 | 910 |
| RC-101-II-2H | Ac—D-Phe—Cys—Phe—D-Trp—Lys—Thr—Cys—Thr—NH$_2$ | 12900 | |
| RC-101-I-2H | Ac—Phe—Cys—Phe—D-Trp—Lys—Thr—Cys—Thr—NH$_2$ | 11320 | |
| RC-159-II | D-Phe—Cys—Tyr—Trp—Lys—Val—Cys—Thr—NH$_2$ (Cys-Cys bridge) | 2380 | |
| RC-160 | D-Phe—Cys—Tyr—D-Trp—Lys—Val—Cys—Trp—NH$_2$ (Cys-Cys bridge) | 13400 | |
| RC-122 | D-Phe—Cys—Tyr—D-Trp—Lys—Val—Cys—Trp—NH$_2$ (Cys-Cys bridge, FOR on Trp) | 4980 | |
| RC-113-2H | D-Phe—Cys—Tyr—D-Trp—Lys—Val—Cys—Tyr—NH$_2$ | 3020 | |
| RC-161 | Ac—D-Phe—Cys—Tyr—D-Trp—Lys—Val—Cys—Thr—NH$_2$ (Cys-Cys bridge) | 5520 | |
| RC-101-I | Ac—Phe—Cys—Phe—D-Trp—Lys—Thr—Cys—Thr—NH$_2$ (Cys-Cys bridge) | 13560 | |
| RC-95-I | D-Phe—Cys—Phe—D-Trp—Lys—Thr—Cys—Trp—NH$_2$ (Cys-Cys bridge) | 5280 | |

Factorial statistical analyses and calculation of potencies in 4 point design assays were carried out by the method of Bliss and Marks (Bliss, C. I. and Marks; H. P.: Quart. J. Pharm. and Pharmacol. 12, 82 and 182, 1946), and Pugsley, (L. I.: Endocr., 39, 161–176, 1946).

In order to determine the time course of the compounds of this invention, male rats are anesthetized with Nembutal and injected with saline or the test octapeptide as in the growth hormone potency assay above. Blood is collected from the jugular vein 15, 30, 45, 60, 90, 120 and 180 minutes post subcutaneous above. This time-course experiment for octapeptides on growth hormone release in vivo a significant suppression of plasma growth hormone. At a dose of 0.1 μg/100 g. administrated subcutaneously, the octapeptide

D-Phe—Cys—Tyr—D-Trp—Lys—Val—Cys—ThrNH$_2$ significantly inhibits growth hormone release for at least 3 hours. At the dose of 2 μg/100 g., the inhibitory effect of somatostatin on growth hormone release is no longer observed after 30 minutes (FIG. 1). The synthetic octapeptides also suppressed growth hormone and prolactin levels in vitro.

The octapeptides of the present invention are also compared to synthetic somatostatin for their ability to inhibit the release of insulin and glucagon in vivo in male rats (CD strain, Charles River) weighing 250–300 g. The rats are kept in controlled temperature (24° C.) and light (0500–1900 h) conditions for 1 week before the assay. Rats are fasted 27–30 hours with free access to water then anesthetized with Nembutal (6 mg/100 g. intraperitoneally). After 30 minutes, saline or test peptide is injected into the jugular vein and blood is collected 5 minutes later from the hepatic portal vein then transferred into chilled tubes containing EDTA (2.5 mg/ml.) and Trasylol (500 K.I.U./ml.). Plasma is separated and stored at −20° C. until assayed for insulin and glucagon. Plasma insulin is determined by double antibody radioimmunoassay using a kit from Cambridge Medical Diagnostics.

Plasma glucagon is determined by the method of Faloona, et al., (1974) In: Methods of Hormone Radioimmunoassay, Eds. Jaffe, B. and Behrman, H. R., Academic Press, New York, pp. 317–330, using crystalline glucagon (Eli Lilly) and rabbit antiserum 30K against glucagon (Unger pool 4, lot 8). Porcine $^{125}$I-glucagon was also purchased from Cambridge Medical Diagnostics, Mass.

In the test systems described above, the octapeptides of the present invention were found to inhibit insulin release in vivo more powerfully than somatostatin on a weight basis (see Table C). Because of the high potency of the octapeptides of the present invention, the absence of toxicity and the long duration of their activity, these octapeptides are useful for application in the treatment of a number of diseases and conditions. For example, the octapeptides of the present invention can be used to assess insulin resistance in obese patients. The use of this compound prevents endogenous insulin secretion. Previously, somatostatin or propranolol were used for this purpose. (Shen, et al., *J. Clin. Invv.*, 49, 2151 (1970)). In this method, to demonstrate total body resistance to exogenous insulin in obese subjects, standard quantities of glucose, insulin and octapeptides are infused for 150 minutes. A steady state level of plasma insulin and glycose should be attained after 90 minutes. Endogenous insulin secretion determined by C-peptide measurement and glucagon secretion remains suppressed throughout the period. With steady state levels of plasma insulin maintained in the subjects, the height of the steady state plasma glucose concentration can be considered an index of total body sensitivity to insulin mediated glucose uptake. A positive correlation between steady state plasma glucose concentration and the degree of obesity can be demonstrated. This is supported by similar studies with somatostatin of Magulesparan et al., *Diabetes*, 28, 980 (1979), but the octapeptides are superior due to their prolonged suppression of insulin.

In diabetic patients who do not produce insulin, by inhibiting growth hormone and glucagon secretion by employing the octapeptides of the present invention, the dose of insulin should be reductible to $\frac{1}{4}$-$\frac{1}{3}$ of that required by the patient in the absence of octapeptides. This is supported by the work of Besser, et al., *Brit. Med. Journal* 4, 622-627 (1974) and Gerich, et al., *Diabetologia*, 13, 537 (1977). These studies utilized somatostatin as an adjunct to insulin. Similarly, the octapeptides of the present invention can advantageously be used in place of somatostatin. In addition, the octapeptides are also useful for treatment of diabetic retinopathy by inhibiting growth hormone secretion which causes vascular damage.

In some patients, after removal of the hypophysis and after bromocryptine treatment, an elevated growth hormone level is still observed. Utilizing the octapeptides of the present invention, in combination with bromocryptine or another similarly effective drug, the growth hormone level is reduced. In addition, LHRH agonists, which given chronically lead to paradoxical inhibitory effects, can also be used. A combined hormonal treatment consisting of octapeptides, LH-RH analogs and bromocryptine can be used for the treatment of acromegaly, while similar combination treatments are useful for other neoplasmas. When the tumors are hormone dependent and these hormones are inhibited by octapeptides, these tumors can be treated with octapeptides. For example, murine and other mammalian chondrosarcomas are growth hormone dependent. Salomon, et al., *Cancer Res.*, 39, 4387 (1979); and McCumbee, *Fed. Proc.*, 30, 428 (1979) reported that rat (Swarm) chondrosarcomas are growth hormone dependent. Human chondrosarcomas are similar to Swarm chondrosarcomas. Somatostatin analogs inhibit the growth of Swarm chondrosarcomas (Redding and Schally, *A.V. Proc. Nat. Acad. Sciences*, 80, 1078-1082 (1983)) and the octapeptides of the present invention are likewise useful for inducing the regression of human chondrosarcoma tumors which cannot be controlled by chemotherapy. Similarly, Dunn-Osteosarcomas C3H/HeJ in mice are similar to human tumors and appear to be hormonally (GH)-dependent (Ghanta et al., *Natl. Cancer Inst.* 57, 837-839 (1976)). Various analogs of somatostatin inhibit the growth of Dunn osteosarcomas (Schally, et al., *Cancer Treatment Reports*, 68, 281, (1984)), Schally, et al., *Proc. Soc. Exp. Med.*, 175, 259 (1984). Octapeptide RC-15,

Ac-D-p-Cl.Phe—Cys—Phe—D-Trp—Lys—Thr—Cys—ThrNH$_2$, at doses of 5 µg/day was found to significantly prolong the survival of mice with Dunn osteosarcomas. Octapeptide RC-121-2H, D-Phe-Cys(SH)-Tyr-D-Trp-Lys-Val-Cys(SH)-ThrNH$_2$, in doses of 2.5 µg/b.i.d. also significantly inhibited growth of Dunn's osteosarcoma tumors of C3H female mice. The % survival was 100%±0.0% as compared to 75%+22% for controls by day 16.

The measurement of antitumor activity of the octapeptides of this invention in an animal mammary cancer model is as follows: Several hormone-dependent mammary tumors in rats and mice have been shown to be estrogen dependent and/or prolactin dependent (Arafah et al., *Endocrinology*, 107, 1364 (1980)); Schally, et al., *Proc. Soc. Exp. Biol. Med.*, 175, 259 (1984). It is known that about $\frac{1}{3}$ of human breast cancers are estrogen dependent. Recent evidence indicates that a significant proportion (30-40%) of human breast cancers may be also prolactin dependent (Malarkey, et al., *J. Clin. Endoc. Metab.*, 56, 673-677 (1983)); Ben, et al., *Israeli J. Med. Sci.*, 17, 965 (1981). In addition, growth hormone is also involved in the growth of breast cancers. The octapeptides of the present invention, by inhibiting prolactin and growth hormone secretion, are useful for inducing regression of human breast carcinomas. The antitumor activity of the octapeptides of the present invention are measured in the MT/W9A rat mammary adenocarcinoma model. The estrogen-dependent MT/W9A rat mammary adenocarcinoma is obtained from Roswell Park Memorial Institute, Bufflao, N.Y. The MT/W9A mammary tumor has been characterized as estrogen-dependent and it needs physiological levels of both prolactin and estrogen for growth (Kim and Depowski, *Cancer Research*, 35, 2068-2077 (1975)). Tumor tissue is minced into approximately 1 mm$^3$ pieces, or until a fine slurry has been made, and injected through an 18 G needle into the inguinal mammary fat pad of female WistarFurth rats (90 gms. body weight). After about 3$\frac{1}{2}$ months the tumors were palpable and the experiment is initiated. Octapeptide RC-15,

Ac-D-p-Cl.Phe—Cys—Phe—D-Trp—Lys—Thr—Cys—ThrNH$_2$, in doses of 3 ug//b.i.d. (twice a day) powerfully inhibited the growth of MT/W9A rat mammary tumor and reduced the percentage change in tumor volume to 1106±447% as compared to 2808±812% for controls, after 16 days of treatment. Thus, the octapeptides of the present invention are utilizable in the treatment of human breast carcinoma. The therapeutic action of octapeptides is due to the inhibition of the growth hormone and prolactin secretion. The octapeptide may be administered alone or in combination with LH-RH analogs such as D-Trp-6-LH-RH, which inhibits the growth of estrogen dependent mammary tumor (Redding and Schally, *Proc. Natl. Acad. Sci.*, USA, 80, 1459–1462 (1983)).

In order to determine activity on pancreatic carcinoma, animal models of pancreatic cancer with acinar and ductal phenotypic characteristics are used. (Redding and Schally, *A. V., Proc. Nat. Acad. Sci.*, 81, 248–252 (1984)). The transplantable well differentiated acinar pancreatic tumors DNCP-322 (CA-20948) in Wistar/Levis rats (Longnecker, et al., *Cancer Research*, 42, 19–24, (1982)); and Longnecker, et al., *Cancer Letters*, 7, 197–202 (1979) are obtained from the Department of Pathology, Dartmouth Medical School, Hanover, N.H. The golden Syrian hamsters bearing the well differentiated (WD), chemically induced ductal adenocarcinoma (Scarpelli, et al., *Cancer Res.*, 39, 452–458 (1979) are used. Donor tumor tissue from either species is quickly dissected and washed in ice cold Hanks buffered saline, pH 7.4 and the capsular material carefully removed. Tumor tissue is then sliced into small pieces and passed through a No. 30 stainless steel screen into a beaker of ice cold buffer. The pellet is resuspended in buffer and 1 to 2 mg. aliquots of tumor tissue injected subcutaneously into the middle back region of weanling male animals of the respective model, i.e., Wistar/Levis rats of LAS Syrian hamsters. Subcutaneously transplanted Longnecker DNCP-322 tumors achieve a diameter of approximately 5 cm in about 4 weeks. WD tumor grows slowly in golden hamsters, tripling its size in about 45 days. In rats bearing the acinar pancreatic tumors, chronic administration of the octapeptides of this invention significantly decreased tumor weights and volume. In Syrian hamsters bearing ductal form of pancreatic cancer, chronic administration of the octapeptides diminished tumor weights and volume (Redding and Schally, *Proc. Nat. Acad. Sci.*, 81, 248–252 (1984)). The percentage change in tumor volume was significantly decreased when compared to control animals. The LHRH agonist D-Trp-6-LH-RH, given twice daily or injected in the form of controlled-release microcapsules significantly decreased tumor weight and volume. The octapeptides reduce the growth of pancreatic ductal and acinar cancers, probably by inhibiting the relase and/or stimulatory action of gastrointestinal hormones, gastrin, secretin and cholecystokinin on tumor cells (Schally, et al., *Proc. Soc. Exp. Biol. Med.*, 175, 259 (1984)). A combined administration of an octapeptide of this invention with an LH-RH agonist leads to a greater inhibition of cancers of the pancreas than that which can be obtained with somatostatin analogs alone.

In order to compare some of the biological actions of the octapeptides of the present invention and somatostatin on gastrointestinal secretions and on the release of some gastrointestinal homones in dogs, the following procedures are used:

Mongrel dogs weighing 15–20 kg. are prepared surgical with gastric (GF) and pancreatic fistulae (PF) as described by Konturek, et al., (1976) 225, 497 and Konturek, et al., *Gastroenterology*, (1976) 58, 1–6. Secretions from the GF and PF are collected continuously at 15 minute intervals. Hydrogen ion and pepsin concentrations in the pancreatic juice are also measured in 15- or 30-minute outputs. (Konturek, et al., *J. Physiol. Lond.*, 255, 497 (1976) and Konturek, et al., (1976) supra.). Basal secretion is first collected for two 15 minute periods, and then the secretory stimulant for gastric and/or pancreatic secretion is administered for $3\frac{1}{2}$ hours. When the secretory rate reaches a subtained plateau, the octapeptides or somatostatin are given in standard doses (2-$\mu$g/Kg/hr.). i.v. for a one hour period. In control experiments, the animals received secretory stimulants along for the duration of the tests.

In tests on gastric stimulation, pentagastrin or desglugastrin (glutaroyl-Ala-Tyr-Gly-Trp-Leu-Asp-Phe-$NH_2$) is infused i.v. in a constant dose (3 $\mu$g/kg/hr.), shown previously to elicit near maximal gastric acid secretion. Gastric secretion is measured and acid content determined by titration with 0.1N NaOH. In tests on pancreatic secretion, synthetic secretion (Squibb and Sons, Inc., New York, N.Y.) and caerulein (Farmitalia, Italy) are used in constant doses shown previously to evoke near maximal stimulation of bicarbonate of pancreatic enzyme secretion (Konturek, et al., (1976) supra.

Experiments on pancreatic stimulation by endogenous stimulants are performed using duodenal instillation of 0.1N HCl or a meat meal (500 g.), (Konturek, et al., (1976) supra). Blood samples are withdrawn before and every 15–20 minutes for serum gastrin determination (Yalow, et al., 58, 1–14 (1970)).

The results observed for the octapeptides of the present invention and somatostatin on gastric acid response to pentagastrin are as follows:

Both the octapeptides and somatostatin administered are found to strongly inhibit pentagastrin or desglugastrin-induced gastric acid output from the GF. The inhibition of acid secretion is more pronounced with the octapeptides. D-p-Cl-Phe-Cys-Tyr-D-TrP-Lys-Val-Cys-ThrNH$_2$ was found to be approximately twice as potent as somatostatin. Moreover, its action was protracted since the inhibition of gastric acid continues after infusion was stopped, in contrast to somatostatin whose action was short-lived.

G.I. tests indicate that the octapeptides are useful for treatment of duodenal ulcers and acute pancreatitis. The octapeptides of this invention or the acid addition thereof are also useful for the treatment of acromegaly and related hypersecretory endocrine states and in the management of diabetes and for the therapy of certain cancers. When the octapeptides or salts thereof are employed for such treatment or management, they are administered systemically, preferably parenterally, or in combination with a pharmaceutically acceptable liquid carrier. The octapeptides of this invention have a low order of toxicity. The proportion of the octapeptide or salt thereof is determined by its solubility in the given carrier, by the given carrier, or by the chosen route of administration. When the octapeptide or a salt thereof is used in a sterile solution, such solution may also contain other solutes such as buffers or preservatives, as well as sufficient amounts of pharmaceutically acceptable salts or glucose to make the solution isotonic. The dosage will vary with the form of administration and with the particular species to be treated. Preferably, the dose range for sublingual or oral administration is about 1 mg. to about 100 mg/kg. of body weight per day. Generally, the dose range for intravenous, subcutaneous or intramuscular administration is from about 0.1 mcg. to about 1 mg/kg. of body weight per day, and, preferably, is from about 0.5 mcg. to about 100 mcg/kg. of body weight per day. It is evident that the dose range will vary widely dependent upon the particular condition which is being treated as well as the severity of the condition.

The octapeptides or salts thereof can be also be administered in one of the long-acting, slow-releasing or depot dosage forms described below, preferably by intramuscular injection or by implantation. Such dosage forms are designed to release from about 0.1 mcg. to about 50 mcg./kg. body weight per day.

It is often desirable to administer the octapeptide continuously over prolonged periods of time in long-acting, slow-release or depot dosage forms. Such dosage forms may either contain a pharmaceutically acceptable salt of the peptide having a low degree of solubility in body fluids, for example, one of those salts described below or they may contain the peptide in the form of a water-soluble salt with a protective carrier which prevents rapid release. In the latter case, for example, the peptide may be formulated with a non-antigenic partially hydrolyzed gelatin in the form of a viscous liquid; or the peptide may be absorbed on a pharmaceutically acceptable solid carrier, for example, zinc hydroxide, and may be administered in suspension in a pharmaceutically acceptable liquid vehicle; or the peptide may be formulated in gels or suspensions with a protective non-antigenic hydrocolloid, for example, sodium carboxymethylcellulose, polyvinylpyrrolidone, sodium alginate, gelatin, polygalacturonic acids, for example, pectin, or certain mucopolysaccharides, together with aqueous or nonaqueous pharmaceutically acceptable liquid vehicles, preservatives, or surfactants. Examples of such formulations are found in standard pharmaceutical tests, e.g., in Remington's Pharmaceutical Sciences, 14th. Ed., Mack Publishing Co., Easton, Pennsylvania (1970). Long-acting, slow-release preparations of the octapeptides of this invention may also be obtained by microencapsulation in a pharmaceutically acceptable containing, for example, gelatin, polyvinyl alcohol or ethyl cellulose, or copolymers of lactic and glycolic acids, poly(d,l-lactide-co-glycolide)microcapsules, cf. T. W. Redding, et al., Proc. Natl. Acad. Sci., USA, 81, 5845–5848 (1984)) and the like.

Further examples of coating materials and of the processes used for microencapsulation are described by J. A. Herbig in "Encyclopedia of Chemical Technology", Vol. 13, 2nd, Ed., pp. 436–456 (1967) Wiley, New York. Such formulations, as well as suspensions of salts of the peptide which are only sparingly soluble in body fluids, for example, salts with pamoic acid or tannic acid, are designed to release from about 0.1 mcg. to about 100 mcg. of the active compound/kg. body weight per day, and are preferably administered by intramuscular injection. Aternatively, some of the solid dosage forms listed above, for example, certain sparingly water-soluble salts or dispersions in or absorbates on solid carriers of salts of the peptides, for example, dispersions in a neutral hydrogel of a polymer of ethylene glycol methacrylate or similar monomers cross-lirked as described in U.S. Pat. No. 3,551,556, may also be formulated in the form of pellets releasing about the same amounts as shown above and may be implanted subcutaneously or intramuscularly.

The invention will appear more fully from the examples which follow. These examples are set forth by way of illustration only and it will be understood that the invention is not to be construed as limited either in spirit or in scope by the details contained therein as many modifications, both in materials and methods will be apparent to those skilled in the art. Throughout these examples the following purification techniques are utilized:

Abbreviations:
HFBA = heptafluorobutyric acid
HPLC = high-performance liquid chromatography
TFA = triluoroacetic acid
UV = ultraviolet For preparing the HPLC eluents, UV grade acetonitrile is purchased from Burdick & Jackson, TFA and HFBA are of Sequanal grade from Pierce and water is double-distilled in glass and passed through a Milli-Q system (Millipore).

High-performance liquid chromatography is carried out on a Waters HPLC system consisting of an M 680 Automated Gradient controller, two M6000A pumps, a U6K injector and a Schoeffell SF 770 variable wavelength UV detector.

Reversed phase HPLC on C18 columns is used both for analyzing and purifying the compounds. The quality and the elution characteristics of the crude peptides are established by analytical HPLC on a Vydac 218TP5 column (4.6 mm×25 cm) using binary gradients of solvent A: 0.1% TFA in water, and solvent B: 0.1% TFA in CH$_3$CN/water 70:30. The good quality of the crude synthetic products combined with optimized separation conditions allows a rapid, one-step purification scheme. Resolution comparable to that of analytical separations was achieved by using a 5 um particle size packing material and a sample load below the capacity of the column. Six to twenty-three mg. of octapeptide is injected in 2–5 mg. portions onto a semi-preparative Vydac 218TP5 column (10 mm×25 cm) and eluted isocratically or by a flat gradient (0.1–0.2% B/min) using the solvent system containing 0.1% TFA, as described below.

For optimal peak "shaving" the main components are collected manually. The volatile eluent is removed by freeze drying and then the products are re-lyophilized from 1M AcOH yielding 0.7 mg (10–45%) of the purified octapeptide. The homogeneity of the octapeptides is checked by analytical HPCL in two different solvent systems (I: 0.1% TFA/CH$_3$CN/water, II: 0.13% HBA/CH$_3$CN/water). Purity using these techniques is better than 90% based on UV absorbance monitored at 210 nm.

EXAMPLE 1

Ac-D-p-Cl.Phe—Cys—Phe—D-Trp—Lys—Thr—Cys—ThrNH$_2$ and

Ac-D-p-Cl.Phe—Cys—Phe—D-Trp—Lys—Thr—Cys—ThrNH$_2$ 0.50 g. benzhydrylamine (BHA) resin (ca. 0.5 NH$_2$/g. resin) is added to a 10 ml. reaction vessel with a special fritter filter of medium porosity, treated with 10% triethylamine in CH$_2$Cl$_2$ two times each for three minutes and washed with CH$_2$Cl$_2$ six times.

The resin is mixed with Boc-Thr(Bz) (0.75 m. moles) and HOBt (0.82 m. moles) in DMF for three minutes. 5% diisopropylcarbodiimide (0.82 m. moles) CH$_2$Cl$_2$ is added. The mixture is shaken at room temperature for 90 minutes. The resulting resin is washed with CH$_2$Cl$_2$ six times and is subjected to a ninhydrin test (Kaiser, et al., *Analytical Biochemistry*, 34, 595 (1970)). It should be negative at this stage.

The deprotection of the Boc- group from Boc-Thr(Bz)-BHA resin is carried out as follows: The resin is treated with a solution of trifluoroacetic acid and methylene chloride (1:1) for 5 minutes, filtered and treated again for 25 minutes, filtered and then washed with $CH_2Cl_2$ six times.

Treatment with 10% triethylamine is performed as described for the benzhydrylamine resin.

The subsequent amino acid residues are then introduced sequentially by coupling in the same manner as described above.

The deprotection is performed as described for Boc-Thr(Bz)-BHA resin. After incorporating Boc-D-Trp, 5% mercaptoethanol is added to 50% trifluoroacetic acid in $CH_2Cl_2$; Boc-D-p-Cl.Phe-Cys(MBz)-Phe-DTrp-Lys(2-ClZ)-Thr(Bz)-Cys(MBz)-Thr(Bz)-BHA; resin is obtained. After deprotection and neutralization, acetylation is done by using ($Ac_2O$) in $CH_2Cl_2$ for 60 minutes (12.5 m. moles).

Finally, the peptide resin is washed with $CH_2Cl_2$, methanol and $CH_2Cl_2$ three time each and dried under vacuum. 0.902 g. Ac-D-p-Cl.Phe-Cys(MBz)-Phe-D-Trp-Lys(2ClZ)-Thr(Bz)-Cys(MBz)-Thr(Bz)-BHA resin is obtained.

500 mg. protected octapeptide BHA resin is mixed with 0.5 ml. cresol and 0.5 ml. 1.2-ethanedithiol, and stirred in 10 ml. hydrogen fluoride at 0° C. for 1 hour. Excess hydrogen fluoride is evaporated under vacuum. The peptide and resin mixture is washed with ethyl acetate and extracted with 30% HOAc and lyophilized. 112 mg. crude product powder consisting of Ac-D-p-Cl.Phe-Cys-Phe-D-Trp-Lys Thr-Cys-Thr-$NH_2$ is obtained.

110 mg. crude reduced form is dissolved in 20 ml. 50% HOAc and diluted to 500 ml. with degassed water ($N_2$), adjusted to pH 6.8 with 28% ammonium hydroxide, then 0.005N potassium ferroxcyanide solution is dropped in with stirring until a permanent yellow color is observed. After stirring for 15 minutes, the pH is readjusted to 5 with HOAc. 5 g. Bio red Ag 3-X 4A resin (chloride form) is introduced to remove ferric and ferrocyanide salts. The filtrate is lyophilized. The residue is subjected to gel filtration on a column (1×120 cm) of Sephadex G15 and eluted with 50% acetic acid. The major peak is lyophilized and 57 mg. of the crude oxidized form, Ac-D-p-Cl.Phe—Cys—Phe—D-Trp—Lys—Thr—Cys—Thr—$NH_2$, is obtained and then purified by chromatography (high pressure liquid chromatography) to give 10.56 mg. pure octapeptide.

EXAMPLE 2

D-Phe—Cys—Tyr—D-Trp—Lys—Val—Cys—Thr—$NH_2$
(reduced form)

and

D-Phe—Cys—Tyr—D-Trp—Lys—Val—Cys—Thr—$NH_2$
(oxidized form).

185 mg. BHA resin (0.5 mm BHA/g. resin) is placed in a 20 ml. reaction vessel which is mounted on a mechanical shaker.

The following amino acid residues, Boc-Thr(Bz), Boc-Cys(MBz), Boc-Val, Boc-Lys(2-ClZ), Boc-D-Trp, Boc-Tyr (2-BrZ), Boc-Cys(MBz), and Boc-D-Phe are introduced sequentially by coupling and deprotection in the same manner as described in Example 1. 330 mg. TFA-D-Phe-Cys(MBz)-Tyr(2-BrZ)-D-Trp-Lys-(2-ClZ)-Val-Cys(MBz)-Thr(Bz)-BHA resin is finally obtained.

The protected octapeptide amide-resin is treated with HF to give 68.1 mg. crude reduced form. The amount of 6.1 mg. crude reduced form is purified by HPLC to give 1.0 mg. pure D-Phe-Cys-Tyr-D-Trp-Lys-Val-Cys-Thr-$NH_2$.40 mg. crude form is oxidized as described in Example 1. The lyophilized powder consisting of oxidized form and salts is subjected to gel filtration with Sephadex G15 and eluted with 50% acetic acid. The major peak is then lyophilized to give 38.1 mg. of which 24.7 mg. is purified by HPCL to afford 9.0 mg. of pure D-Phe—Cys—Tyr—D-Trp—Lys—Val—Cys—Thr—$NH_2$.

EXAMPLE 3

Ac-D-Phe—Cys—Phe—D-5F—Trp—Lys—Thr—Cys—ProNH$_2$ and

Ac-D-Phe—Cys—Phe—D-5F—Trp—Lys—Thr—Cys—ProNH$_2$ 230 mg. benzhydrylamine resin (ca. 0.5 mm BHA/g. resin) is placed in a 5 ml. reaction vessel which is mounted on a mechanical shaker. The protected octapeptide resin is obtained after stepwise coupling of the following:

Boc-Pro, Boc-Cys(MBz), Boc-Thr(Bz), Boc-Lys(2-ClZ), Boc-D/L-5F-Trp, Boc-Phe, Boc-Cys(MBz), Boc-D-Phe.

Acetylation is done after the last deprotection. 351 mg. Ac-D-Phe-Cys(MBz)-Phe-D/L-5F-Trp-Lys(2ClZ)-Thr(Bz)-Cys(MBz)-Pro-BHA resin is finally obtained and treated with HF to give 74.5 mg. crude reduced form. The crude peptide in reduced form is oxidized as described in Example 1. After gel filtration, further purification and separation of D/L diastereomers is performed by HPLC.

EXAMPLE 4

D-Phe—Cys—Tyr—D-5F—Trp—Lys—Val—Cys—Thr—$NH_2$ and

D-Phe—Cys—Tyr—D-5F—Trp—Lys—Val—Cys—Thr—$NH_2$ 200 mg. benzhydrylamine resin (ca. 0.36 m. mol. NH₂/g. resin) is placed in a shaking reaction vessel. After addition of the protected amino acids, TFA-D-Phe-Cys(MBz)-Tyr(2-BrZ)-D/L-5F-Trp-Lys(2-ClZ)-Val-Cys(MBz)-Thr(Bz)-BHa resin (394 mg.) is obtained. The protected resin is treated with HF to give 97.5 mg. crude peptide of D-Phe-Cys-Tyr-D/L-5F-Trp-Lys-Val-Cys-Thr-NH₂ (in reduced form). 80 mg. of crude reduced form is oxidized as described in Example 1. After gel filtration, Peaks I and II are lyophilized, yielding 19.8 mg. respectively. Further purification and separation of D/L diastereomers is performed by HPLC.

EXAMPLE 5

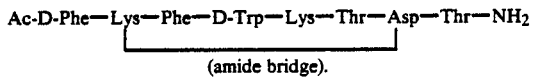

512 mg. Ac-D-Phe-Lys(2-ClZ)-Phe-D-Trp-Lys(TFA)-Thr(Bz)-Asp(OBz)-Thr(Bz)-BHA resin is obtained from 320 mg. benzhydrylamine resin. (TFA=trifluoroacetyl) The protected peptide resin is treated with HF to give 127 mg. crude peptide of Ac-D-Phe-Lys-Phe-D-Trp-Lys(TFA)-Thr-Asp-Thr-NH₂. The cyclization procedure is as follows:

100 mg. crude peptide of Ac-D-Phe-Lys-Phe-D-Trp-Lys-Thr(TFA)-Asp-Thr-NH₂ and 50 mg. HOBT are dissolved in 4 ml. DMF and 0.2 m mol. N,N-diisopropylcarbodiimide in CH₂Cl₂ is added to the solution with stirring at 0° C. for 2 hours and at room temperature for 5 hours until a negative ninhydrin test is obtained. The solvent is evaporated under vacuum. Removal of TFA-group of Lys in the peptide is performed in a solution of piperidine:DMF:H₂O=10:45:45 by stirring at room temperature for 3 hours. The DMF and piperidine are removed by evaporation. The oily material is subjected to gel filtration on Sephadex G15 (1×120 cm). The peaks I and II are lyophilized to give 30 mg. and 48.4 mg., respectively. The peak II is purified by HPLC to give 25 mg. pure peptide of

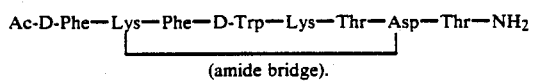

EXAMPLE 6

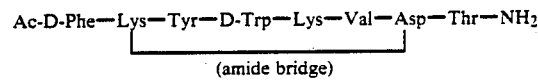

The synthesis route is described in the following scheme:

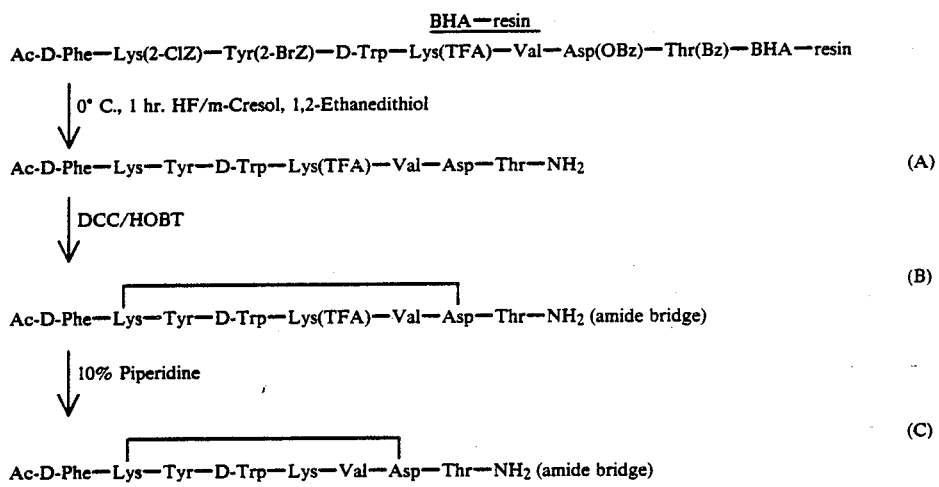

Procedure:

2.14 g. Ac-D-Phe-Lys(2-ClZ)-Tyr(2-BrZ)-D-Trp-Lys(TFA)-Val-Asp(OBz)-Thr(Bz)-BHA-resin is obtained from 1.5 g. benzhydrylamine resin (0.26 m. mol/g.). The protected peptide resin is treated with HF to give 279 mg. crude peptide of Ac-D-Phe-Lys-Tyr-D-Lys(TFA)-Val-Asp-Thr-NH₂ (A).

40 mg. crude peptide (A) is purified by HPLC. The rest of crude peptide (A) is cyclized with diisopropylcarbodiimide and HOBT using the same procedure as described in Example 5.

One sixth of the reaction mixture of Ac-D-Phe-Lys-Tyr-D-Trp-Lys(TFA)-Val-Asp-Thr-NH₂ (B) is subjected to gel filtration on Sephadex G15 (1×120 cm) and eluted by 30% acetic acid. HPLC is used as a guide to combine the peaks separately. The peptide eluted is lyophilized and purified by HPLC to give pure peptide (B). The rest of the reaction mixture is dissolved in a solution of piperidine: DMF:H₂O=10:45:45 and stirred at room temperature for 3 hours. The solvent is evaporated under vacuum. The oily material is subjected to gel filtration on Sephadex G15 (1×120 cm) and eluted with 30% acetic acid. The Peaks I and II are lyophilized to give 58.3 mg. and 127.3 mg. respectively. Further purification of peak II is performed by HPLC to give 80 mg. pure peptide (C),

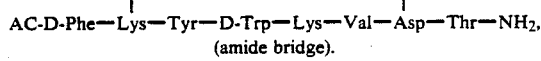

EXAMPLE 7

D-Trp—Cys—Phe—D-Trp—Lys—Thr—Cys—Thr—NH₂
(reduced form)

and

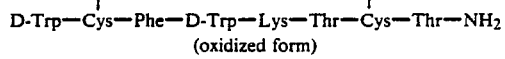
(oxidized form)

292 mg. TFA-D-Trp-Cys (MBz)-Phe-D-Trp-Lys(2-ClZ)Thr(BZ)-Cys(MBz)-Thr(Bz)-BHA resin was obtained from 150 mg. BHA resin (0.5 mmBHA/g. resin) after stepwise coupling. The protected octapeptide amide-resin was treated with HF to give 72.8 mg. crude reduced form. The amount of 22.5 mg. crude reduced form was purified by HPLC to afford 8.0 mg. pure D-Trp-Cys-Phe-D-Trp-Lys-Thr-Cys-Thr-NH$_2$ (RC-98-I-2H).

The oxidation of reduced form was carried out with iodine because of its poor solubility under the conditions used for oxidation with potassium ferricyanide. The procedure is described in the following:

50 mg. crude reduced form was dissolved in 100 ml. 95% AcOH, then 0.005M iodine solution in glacial AcOH was dropped in until the yellow color persisted. Excess iodine was removed by adding zinc powder. After oxidation, the crude disulfide peptide was subjected to gel filtration on Sephadex G15 column. In the cases of octapeptides containing two Trp residues, a two-step elution was used. The crude oxidized product was dissolved in 50% AcOH and applied onto the Sephadex column that had been equilibrated with water. The salts were washed off the column with water, then the peptide was eluted and fractionated using 50% AcOH. The major peak was lyophilized and 30 mg. crude oxidized product was obtained. Further purifications was performed by semipreparative HPLC to afford 9.4 mg. of pure

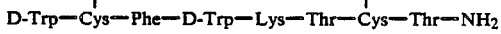

The purified octapeptide was characterized by amino acid analyses and analytical HPLC showed the expected results.

SOMATOSTATIN ANALOGS POTENCY ASSAY #1
(The 89th. Experiment, July 12, 1985)

| Code | Injected Dose (μg/100 g. B.W.) | GH Level (ng/ml) 15' | 30' | 60' |
|---|---|---|---|---|
| CONTROL | 0.2% Bovine Serum Albumin | 116 ± 10 | | |
| SS-14 (Somatostatin #14) | 0.4 | 88 ± 22 | | |
| SS-14 | 1.6 | 53 ± 10 | | |
| RC-98.I.2H | 0.02 | 50 ± 10 | | |
| RC-98.I.2H | 0.08 | 28 ± 4 | | |

RC-98.I.2H vs. SS-14: M = 0.6653, Antilog M = 4.63, Potency = 92.6 times vs. SS-14.

SOMATOSTATIN ANALOGS POTENCY ASSAY #2
(The 108th. Experiment, Jan 16, 1986)

| Code | Injected Dose (μg/100 g. B.W.) | GH Level (ng/ml) 15' | 30' | 60' |
|---|---|---|---|---|
| CONTROL | 0.2% Bovine Serum Albumin | 211 ± 56 | | |
| SS-14 (Somatostatin #14) | 0.2 | 171 ± 26 | | |
| SS-14 | 0.8 | 91 ± 12 | | |
| RC-98-I | 0.01 | 85 ± 16 | 72 ± 8 | 182 ± 25 |
| RC-98-I | 0.04 | 52 ± 4 | 38 ± 3 | 100 ± 26 |

| CODE | POTENCY % 15' | 30' |
|---|---|---|
| RC-98-I vs. SS-14 | 9139.65 (2864.7–29159.5) | 12388.8 (3883.28–39524.2) |

SOMATOSTATIN ANALOG POTENCY #3

| CODE | INJECTED DOSE | GH-RH LEVEL |
|---|---|---|
| SS-14 | 2.0 | 0.1032 |
| RC-98-I | 0.1 | 0.4340 |

RC 98-I vs. SS-14 Potency* = 84.1 times vs. SS-14
*Based on time course of CPZ and Morphine - stimulated GH secretion.

As shown in FIG. I, it will be understood that the rebound of SS-14 on the Control line is highly undesirable.

EXAMPLE 8

In a similar manner, utilizing the techniques and procedures described in Examples 1–7, there are obtained the following compounds of this invention:

TABLE 1

Formula (I) and (I')
A. Cys. Phe. D-Trp. Lys. Thr. Cys. B (I) (reduced form)

A. Cys. Phe. D-Trp. Lys. Thr. Cys. B (I') (oxidized form)

| A | B | Formula |
|---|---|---|
| D-Ala | Thr NH$_2$ | I |
| D-Val | " | " |
| Ac.Phe | " | " |
| D-Phe | " | " |
| D-Phe | " | I' |
| Ac.D-Phe | " | I |
| p.Cl.D-Phe | " | " |
| p.Cl.D-Phe | " | I' |
| Ac.p.Cl.D-Phe | " | I |
| Ac.p.Cl.D-Phe | " | I' |
| Ac.Trp | " | I |
| Ac.Trp(For) | " | " |
| Ac.D-Trp | " | " |
| D-Trp | " | " |
| Ac.Pro | " | " |
| D-Pro | " | " |
| Ac.Pro(OH) | " | " |
| Ac.Ser | " | " |
| D-Ser | " | " |
| Ac.Thr | " | " |
| D-Thr | " | " |
| Ac.Tyr | " | " |
| Dp—Glu | " | " |
| Ac.D-Phe | Val NH$_2$ | " |
| Ac.D-Phe | Pro NH$_2$ | " |
| D-Ser | (HO)Pro NH$_2$ | " |
| D-Phe | (HO)Pro NH$_2$ | I |
| D-Ser | " | " |
| D-Phe | D-Ser NH$_2$ | " |
| D-Phe | Tyr NH$_2$ | " |
| Ac.D-Phe | Trp NH$_2$ | " |
| " | D-Trp NH$_2$ | " |
| " | D/L 5F Trp NH$_2$ | " |

TABLE 1-continued

Formula (I) and (I')
A. Cys. Phe. D-Trp. Lys. Thr. Cys. B (I) (reduced form)

A. ⌐Cys. Phe. D-Trp. Lys. Thr. Cys.¬ B (I') (oxidized form)

| A | B | Formula |
|---|---|---|
| Ac.Trp(For) | For–Trp NH$_2$ | " |
| " | D/L 5F Trp NH$_2$ | " |
| Ac.D-Trp | D-Trp NH$_2$ | " |
| " | For–Trp NH$_2$ | " |
| Ac.Trp | D-Trp NH$_2$ | " |
| Ac. Trp(For) | Pro NH$_2$ | " |
| p.Cl D-Phe | " | " |
| Ac.Pro | " | " |
| D-Ser | " | " |
| Ac.Pro | For–Trp NH$_2$ | " |
| Ac.D-Phe | " | " |
| Ac D/L 5F Trp | Thr NH$_2$ | " |

TABLE 2

Formula (II) and (II')
A. Cys. Tyr. D-Trp. Lys. Val. Cys. B (II)

A. ⌐Cys. Tyr. D-Trp. Lys. Val. Cys.¬ B (II')

| A | B | Formula |
|---|---|---|
| Ac.Gly | Thr NH$_2$ | II |
| D-Val | " | " |
| Ac.Phe | " | " |
| D-Phe | " | " |
| D-Phe | " | II' |
| Ac.D-Phe | " | II |
| Ac.D-Phe | " | II' |
| p.Cl.D-Phe | " | II |
| " | " | II' |
| Ac.Pro | " | II |
| D.Pro | " | " |
| Dp—Glu | " | " |
| D-Glu | " | " |
| D-Trp | " | " |
| Ac.Ser | " | " |
| D-Ser | " | " |
| D-Tyr | " | " |
| D-Ala.Phe | " | " |
| D-Phe | Thr Ala NH$_2$ | " |
| " | Ala NH$_2$ | " |
| " | Gly NH$_2$ | " |
| " | Me Ala NH$_2$ | " |
| " | Abu—NH$_2$ | " |
| p.Cl.D-Phe | Ala NH$_2$ | " |
| D-Phe | Pro NH$_2$ | " |
| " | D-Pro NH$_2$ | " |
| D-Phe | (HO)Pro NH$_2$ | " |
| Ac—LPhe | " | " |
| D-Phe | Tyr NH$_2$ | " |
| " | Ser NH$_2$ | " |
| " | " | II' |
| D-Ser | Ala NH$_2$ | " |
| " | (HO)Pro NH$_2$ | " |
| " | Ser NH$_2$ | " |
| " | Tyr NH$_2$ | " |
| D-Val | Ala NH$_2$ | " |

TABLE 2-continued

Formula (II) and (II')
A. Cys. Tyr. D-Trp. Lys. Val. Cys. B (II)

A. ⌐Cys. Tyr. D-Trp. Lys. Val. Cys.¬ B (II')

| A | B | Formula |
|---|---|---|
| D-Phe | For–Trp NH$_2$ | " |
| D-Phe | " | " |
| p.Cl D-Phe | " | II |
| D-Val | " | " |
| Ac.Pro | " | " |
| Ac.Trp(For) | D/L 5F Trp NH$_2$ | " |
| D-Phe | " | " |
| " | " | II' |
| " | Trp NH$_2$ | II |
| " | " | II |

TABLE 3

Formula (III) and (IV')
A. Cys. Phe. Z. Lys. Thr. Cys. B (III)

A. ⌐Cys. Phe. Z. Lys. Thr. Cys.¬ B. (III')

A. Cys. Tyr. Z. Lys. Val. Cys. B. (IV)

A. ⌐Cys. Tyr. Z. Lys. Val. Cys.¬ B. (IV')

| A | B | Z | Formula |
|---|---|---|---|
| Ac. p.Cl.D-Phe | Thr NH$_2$ | D/L 5F Trp | III |
| Ac.D-Phe | Pro NH$_2$ | D-Trp | " |
| " | " | Trp | " |
| | | For–Trp | |
| " | " | D/L 5F Trp | " |
| Ac.D-Phe | " | " | III' |
| D-Phe | " | " | III |
| Ac.p.Cl.D-Phe | " | " | " |
| D-Phe | (HO)Pro NH$_2$ | " | " |
| D-Ser | " | " | " |
| p.Cl.D-Phe | Thr NH$_2$ | " | IV |
| D-Phe | " | " | " |
| " | " | " | IV' |
| " | " | Trp | IV |
| " | " | " | IV |

TABLE 4

Formula (V) and (VI)

A. ⌐C". phe. D-Trp. Lys. Thr. C'.¬ B (V)

A. ⌐C".Tyr. D-Trp. Lys. Val. C'.¬ B (VI)

| A | B | C" | C' | Formula |
|---|---|---|---|---|
| D-Phe | Thr NH$_2$ | Cys | Cys | V |
| " | " | D Cys | D Cys | " |
| " | " | D Cys | Cys | " |
| " | " | Cys | D Cys | " |
| Ac.D-Phe | " | Lys | Asp (amide br) | " |
| " | " | " | " | VI |

TABLE 5

Calculation of Gastric and Inhibitory Activity of Octapeptide RC-88-II = p-Cl—D-Phe—Cys—Tyr—D-Trp—Lys—Val—Cys—Thr—NH$_2$ on the Basis of 16 Experiments in Dogs with Gastric Fistulae.

| Raw Data Standard Dose | | Tested Material Dose | |
|---|---|---|---|
| Low | High | Low | High |
| 3 | 6 | 3 | 6 |
| 49 | 23.6 | 22.5 | 12 |
| 48 | 25.8 | 23 | 9 |
| 71 | 35.9 | 35.6 | 27 |
| 53 | 27 | 22.8 | 16 |

| | Sum Of Squares | DF | Mean Square | F Ratio |
|---|---|---|---|---|
| Row (Material) | 1709.82 | 1 | 1709.82 | 27.6527 |
| Column (Dose) | 1380.12 | 1 | 1380.12 | 22.3205 |
| Interaction | 295.839 | 1 | 295.839 | 4.78456 |
| Subtotal within | 3385.79 | 3 | 1128.6 | |
| Doses | 741.984 | 12 | 61.185 | |
| Total: | 4127.77 | 15 | 275.185 | |

SDT ERROR: 7.86333
VALUES

| | | |
|---|---|---|
| ROW (Samples) | 27.6527 | SIGNIFICANT |
| COLUMN (Slope) | 22.3205 | " |
| INTERRACTION (Parallel) | 4.78458 | " |

SAMPLE POTENCY = 216.303%
POTENCY RANGE FROM 140.669% to 332.605%
LAMBA (Degrees of Precision) = .234861E-01

We claim:

1. A compound of the formula

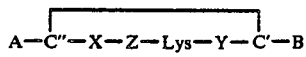 (I)

wherein

A is an L, D or DL amino acid selected from the group consisting of tryptophan (Trp), its acetylated derivatives or a pharmaceutically acceptable acid addition salt thereof;

B is an L, D or DL amino acid selected from the group consisting of threonine amide (Thr NH$_2$), tyrosine amide (Tyr NH$_2$) and tryptophan amide (Trp NH$_2$);

X is L-phenylalanine (L-Phe) or L-tyrosine (L-Tyr);
Y is L-valine (L-Val) or L-threonine (L-Thr);
Z is D-tryptophan (D-Trp); and
C" and C' are L or D-cysteine (Cys), α-aminobutyric acid (Abu), aspartic acid (Asp) or lysine (Lys); provided that where C' is Cys, C" is also Cys and where C' or C" are other than Cys, C" is different from C' and is other than Cys; the connecting line between C" and C' signifies a bridge selected from the group consisting of carbon/carbon, carbon/sulfur, sulfur/sulfur and amide bridges; and the pharmaceutically acceptable acid addition salts thereof.

2. A compound according to claim 1 wherein
C" is Cys;
X is Phe;
Z is D-Trp;
Y is Thr; and
C' is Cys.

3. A compound according to claim 1 wherein
C" is Cys;
X is Phe;
Z is D-Trp;
Y is Thr;
C' is Cys; and
A is D-Trp.

4. A compound according to claim 1 wherein
C" is Cys;
X is Tyr;
Z is D-Trp;
Y is Val; and
C' is Cys.

5. A compound according to claim 1 wherein
C" is Cys;
X is Phe;
Y is Thr; and
C' is Cys.

6. A compound according to claim 1 wherein
C" is Cys;
X is Tyr;
Y is Val; and
C' is Cys.

7. A compound according to claim 1 wherein
C" is Lys;
X is Tyr;
Z is D-Trp;
Y is Val; and
C' is Asp.

8. A compound according to claim 1 which is D-Trp-Cys-Tyr-D-Trp-Lys-Val-Cys-Thr-NH$_2$.

9. A compound according to claim 1 which is:

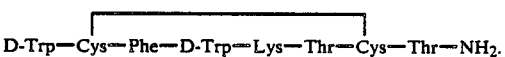

10. An octapeptide (reduced form) of the formula

A-C"-X-Z-Lys-Y-C'-B    (I')

11. A compound according to claim 10 which is:

D-Trp-Cys-Phe-D-Trp-Lys-Thr-Cys-Thr-NH$_2$.

12. A compound which is:

D-Phe-Cys-Tyr-D-Trp-Lys-Val-Cys-Ser-NH$_2$.

13. A pharmaceutical composition which comprises an octapeptide of claim 1 its reduced form or a pharmaceutically acceptable acid addition salt thereof in a pharmaceutically acceptable liquid or solid carrier thereof.

14. A pharmaceutical composition of claim 13 which comprises an octapeptide of claim 1, its reduced form or a pharmaceutically acceptable acid addition salt thereof, encapsulated in poly(d,1-lactide-co-glycolide)-microcapsules.

15. A method of treating excess release of growth hormone, gastrointestinal disorders, and diabetes in a mammal in need of such therapy which comprises administering to said mammal an effective dose of octapeptide of claim 1, its reduced form, or a pharmaceutically acceptable acid addition salt thereof.

* * * * *